(12) United States Patent
Keränen et al.

(10) Patent No.: US 11,382,748 B2
(45) Date of Patent: Jul. 12, 2022

(54) DEVICE AND METHOD FOR IMPROVING FIXATION OF A MEDICAL DEVICE

(71) Applicant: Medtentia International Ltd. Oy, Espoo (FI)

(72) Inventors: Olli Keränen, Bjärred (SE); Hans-Reinhard Zerkowski, Riehen (CH)

(*) Notice: Subject to any disclaimer, the term of this patent is extended or adjusted under 35 U.S.C. 154(b) by 0 days.

(21) Appl. No.: 16/560,908

(22) Filed: Sep. 4, 2019

(65) Prior Publication Data

US 2020/0093598 A1 Mar. 26, 2020

Related U.S. Application Data

(63) Continuation of application No. 14/357,764, filed as application No. PCT/EP2012/072285 on Nov. 9, 2012, now abandoned.

(60) Provisional application No. 61/559,689, filed on Nov. 14, 2011.

(30) Foreign Application Priority Data

Nov. 12, 2011 (EP) ...................................... 1188915

(51) Int. Cl.
*A61F 2/24* (2006.01)
(52) U.S. Cl.
CPC .......... *A61F 2/2445* (2013.01); *A61F 2/2409* (2013.01); *A61F 2/2448* (2013.01); *A61F 2/2466* (2013.01); *A61F 2/2403* (2013.01); *A61F 2/2454* (2013.01); *A61F 2230/0091* (2013.01); *A61F 2240/002* (2013.01); *A61F 2250/006* (2013.01); *Y10T 29/49801* (2015.01)

(58) Field of Classification Search
None
See application file for complete search history.

(56) References Cited

U.S. PATENT DOCUMENTS

| 4,164,046 A | 8/1979 | Cooley |
| 2005/0256567 A1 | 11/2005 | Lim et al. |
| 2007/0179604 A1 | 8/2007 | Lane |
| 2010/0145440 A1* | 6/2010 | Keranen ............... A61F 2/2448 623/2.37 |

FOREIGN PATENT DOCUMENTS

| CN | 101588771 A | 11/2009 |
| CN | 102247225 A | 11/2011 |
| EP | 0338994 A1 | 10/1989 |

(Continued)

*Primary Examiner* — Leslie Lopez
(74) *Attorney, Agent, or Firm* — Patent Grove LLC; Tomas Friend

(57) ABSTRACT

A device for improving the function of a heart valve comprises a first loop-shaped support, which is configured to abut a first side of the heart valve. A first flange unit is may be configured as a fabric sleeve covering the loop-shaped support. A portion of the fabric sleeve forms a flange that is attached to the annulus when said first loop-shaped support is abutting said heart valve. The flange is provideable by folding at least a portion of said sleeve over itself for forming a double layer of opposing fabrics thereof, such that said sleeve comprises a flange portion extending from said first loop-shaped support configured to overlap a surface of and form a collar around, at least a portion of said annulus.

11 Claims, 10 Drawing Sheets

(56) References Cited

FOREIGN PATENT DOCUMENTS

| JP | 2011506017 A | 3/2011 |
|---|---|---|
| WO | WO2002/049546 A2 | 6/2002 |
| WO | WO2008/058940 A1 | 5/2008 |

* cited by examiner

DEVICE AND METHOD FOR IMPROVING FIXATION OF A MEDICAL DEVICE

RELATED APPLICATIONS

This application is a continuation of U.S. patent application Ser. No. 14/357,764, filed May 12, 2014, entitled Device And Method For Improving Fixation Of A Medical Device, which is a U.S. National Phase application of and claims priority to International Patent Application No. PCT/EP2012/072285, International Filing Date Nov. 9, 2012, entitled Device And Method For Improving Fixation Of A Medical Device; which claims benefit of European Application No. EP11188915.0, filed Nov. 12, 2011 entitled Device And Method For Improving Fixation Of A Medical Device; and U.S. Provisional Application Ser. No. 61/559,689, filed Nov. 14, 2011 entitled Device And Method For Improving Fixation Of A Medical Device; all of which are incorporated herein by reference in their entireties.

FIELD OF THE INVENTION

The present invention pertains in general to the field of fixation of medical devices, such as implants to body tissue at a patient. Some particular examples are related to repair or replacement of heart valves having various malformations and dysfunctions. More specifically, some aspects of the invention relate to or are useful in heart valve repair techniques and/or medical procedures involving annuloplasty devices.

BACKGROUND OF THE INVENTION

Medical devices frequently need to be fixated to body parts of a patient. For instance, diseased mitral and tricuspid valves frequently need replacement or repair. The mitral and tricuspid valve leaflets or supporting chordae may degenerate and weaken or the annulus may dilate leading to valve leak, i.e. an insufficiency of valve function. The leaflets and chords may become calcified and thickened rendering them stenotic, which implies obstructing a forward flow through the valve. Finally, the valve relies on insertion of the chordae inside the ventricle. If the ventricle changes in shape, the valve support may become non-functional and the valve may leak. Mitral and tricuspid valve replacement and repair are traditionally performed with a suture technique.

During heart surgery, a premium is placed on reducing the amount of time used to replace and repair valves as the heart is frequently arrested and without perfusion. In U.S. Pat. No. 6,368,348, for example, an annuloplasty prosthesis is disclosed for supporting an annulus of a heart valve. A biological tissue material covering may be provided tightly covering an interior carrier, preferably in its entirety (see e.g. claim 36 of U.S. Pat. No. 6,368,348). The prosthesis is devised to be stitched to the annulus of the heart thus remodelling the same.

United States Patent application no. US 2002/0173841 and U.S. Pat. No. 6,419,696, which are assigned to the same assignee as the present application, disclose an annuloplasty device comprising a first and a second support ring, which are connected to each other to form a coiled configuration. The first and second support rings are arranged to abut opposite sides of a valve annulus to trap valve tissue between them. This annuloplasty device may be easily applied to the valve by rotating the device into position on opposite sides 15 of the valve annulus. To ensure a proper and lasting fixation to the valve annulus such device can be fixated by barbs, retaining members, interlocking portions, fastener s or locking elements, all being integrated in the device. Fixation can also be accomplished by means of suturing. Paravalvular leakage is 20 another issue that is however not addressed in these disclosures.

United States Patent application no. US-2010-0145440-A1 of the same patent proprietor as the present disclosure discloses a device for improving the function of a heart valve that 25 comprises a first loop-shaped support, which is configured to abut a first side of the heart valve, and a first flange unit being connected to said first loop-shaped support. The flange unit is configured to be arranged against said annulus when said first loop-shaped support is abutting said heart valve. The 30 flange unit may provide sealing and deals thus with paravalvular leaks.

However, the prosthetic devices disclosed in the above mentioned documents might be further improved for a more convenient, faster positionable, and/or even more reliable device and method of valve repair and valve replacement. It is a specific object of the invention to provide an alternative device, which allows for an easy and durable fixation to the valve annulus.

Furthermore, a desired improvement to be provided by improved devices and methods comprises allowing a prevention or minimization of backflow of blood, e.g. passing by or underneath the prosthetic devices of the prior art. Hence, an improved annuloplasty device and medical procedure would be advantageous, particularly one allowing for increased flexibility, cost-effectiveness, convenience and speed 15 of positioning, increased reliability and/or patient safety.

BRIEF SUMMARY OF THE INVENTION

An object of the invention is to provide an improved medical device and method of valve repair and valve replacement. Another object of the invention may be to provide an annuloplasty device, which allows for an easy and durable fixation to the valve annulus.

Accordingly, embodiments of the present invention preferably seek to mitigate, alleviate or eliminate one or more 25 deficiencies, disadvantages or issues in the art, such as the above-identified, singly or in any combination by providing a medical device and a method according to the appended patent claims.

According to a first aspect of the invention, there is provided a medical device for improving the function of a heart valve comprised of valve tissue including an annulus and a plurality of leaflets, the device comprising: a first loop-shaped support, which is configured to abut a first side of the heart valve, and a fabric sleeve at least partly covering said first loop-shaped support, and which sleeve is sized to be folded over itself for forming at least a first flange unit.

This device may be used to perform annuloplasty, i.e. to reshape the valve annulus, in order to improve the function of the valve. The flange unit provides a well defined surface to be used when fixating the device against the annulus no matter if the device in use is positioned abutting the atrial or the ventricle side of annulus. This implies that the device may easily be fixated to the annulus in a speedy manner. This is of importance since, during heart surgery, a premium is placed on minimizing time used to replace and repair valves as the heart is frequently arrested and without perfusion.

Also, the flange unit may provide for a sealing surface against said annulus allowing prevention of backflow of blood from the ventricle side to the atrial side.

In addition, the flange unit may be used for carrying or fixation of a prosthetic valve.

The sleeve may comprise a flange portion extending from said first loop-shaped support configured to overlap a surface of, and form a collar around, at least a portion of said annulus. The sleeve may comprise a casing port on configured to cover said first loop-shaped support and a flange portion extending from said casing portion and configured to overlap a surface on the annulus.

The flange formed is in embodiments formed of a double layer of opposed fabrics of said sleeve.

In some embodiments, the flange is arranged radially outwards from said loop-shaped support.

The device may further comprise a second loop-shaped support, which is configured to abut a second side of the heart valve opposite to said first side, whereby a portion of the valve tissue is trapped between the first and second supports. The trapping of valve tissue between the first and second loop-shaped supports implies that the desired shape of the valve, whether natural or prosthetic, may be fixated. Further the trapping implies that the device may temporarily be kept in correct position while fixating the device permanently to an annulus by means of e.g. sutures or clips.

The first loop-shaped support may be formed continuously with the second loop-shaped support to form a substantially coil-shaped body. This implies that the device and its coil-shape may be applied at a commissure between the leaflets of the heart valve and be rotated approximately 360° such that one loop-shaped support is inserted through the commissure to extend along one side of the valve and the other loo-shaped support is arranged along the opposite side of the valve. Thus, valve tissue will be trapped between the supports to fixate a desired shape of the valve. Depending on the extension of the flange means, the latter may provide an attachment surface on one of or on both sides of the annulus for fixation of the device.

The first flange unit may extend from the first loop-shaped support to the second loop-shaped support, whereby the flange unit may be configured to be arranged against the annulus on opposite sides of the valve tissue being trapped between the first and second supports. This implies that the flange unit may form a flange surface on both sides of the annulus or heart valve, which surface may provide for fixation, not only of the device but also of a prosthetic valve. Further, the flange unit may form a sealing surface that, depending on the position of the device, allows reduction or prevention of possible backflow of blood from the ventricle side to the atrial side.

The second loop-shaped support may comprise a second flange unit being connected thereto, which flange unit may be configured to be arranged against the annulus on a side thereof being opposite the first loop-shaped support when the second 5 loop-shaped support is abutting the heart valve. This allows prevention of paravalvular leakage.

At least one of the first and second flange units may be adapted to form a connection of at least one of the loop-shaped supports and a prosthetic valve against the annulus. This implies a rapid fixation, which is of importance since during heart surgery a premium is placed on reducing the time required.

At least one of the first and second flange units may have an intermittent or continuous extension along the periphery of its corresponding loop-shaped support. By way of example, in case of an intermittent extension, the flange unit may be formed by two local sections diametrically opposing each other, whereby the two sections, when the device is positioned in the heart valve, are abutting the commissures and form a sealing surface thereto.

At least one of the first and second flange units may be made of a fabric material. The fabric material may be a woven material. A fabric has the advantage that it presents a rough surface enhancing ingrowth or anchoring of endothelia. Further, a fabric is easily penetrated by sutures or clips. Also, a fabric allows the flange unit to be easily conformed to the annulus.

The fabric material may be impregnated with or integrate a pharmaceutical agent further improving embodiments of the devices and method. The pharmaceutical agent may for instance be an anti inflammatory, stenos preventing, or endotheliazation promoting agent.

Further, at least one of the first and second flange units may comprise a reinforcing element. The reinforcing element provides an indication and definition of an area in which clips or sutures are to be put when fixating the medical device to the annulus. Further, the reinforcing element contributes to reducing the risk of pockets being formed along the circumferential surface. Also, the element prevents unthreading of the fabric in the flange.

At least one of the first and second flange unit may protrude or extend out from and form an angle α (see e.g. FIG. 5) of approximately 30-60°, such as e.g. approximately 40-50° below a diametric plane formed by one of the loop-shaped supports. By the flange unit initially extending below the diametric plane, the visibility during insertion is enhanced. In some embodiments, during insertion, the flange unit due to inherent flexibility may be folded, e.g. downwards in FIG. 5, even folded back over its point of fixation relative the diametric plane, or above the diametric plane with an outer edge of the flange unit. The point of fixation of at least one of the flange unit may be fixed in relation to the diametric plane, radially outward from at least one of the loop-shaped supports.

The flange unit may protrude with other angles, even in a fold back, i.e. more than 90°. This may be during or prior to a time of use or implantation thereof. The angle may be variable over time, e.g. to the herein described shape memory effect of some embodiments of the flange unit.

The flange unit may in some embodiments be arranged to change shape during insertion, e.g. by a resilient arrangement thereof. The flange unit may also be made of a shape memory material that returns to a pre-defined shape of form during insertion of the medical device, e.g. by a temperature triggered effect as known in the art of shape memory materials.

At least one of the first and second flange units extends radially inwards or outwards from its corresponding loop-shaped support. A radially inward extension provides a support for the valve leaflets, whereas a radially outward extension provides a support against the annulus. The first side of the heart valve is the atrial side and the second side is the ventricle side.

At least one of the first and second flange unit or a flange unit extending over first and second loop-shaped supports may be a sleeve covering the first and/or second loop-shaped support. The sleeve comprises a sealing fabric portion that can be drawn radially outward from the loop-shaped support and is configured to be squeezed or flattened to form a collar that is used to fixate (or attach) the device to the valve tissue. For example the sleeve may be drawn rad ally away from the loop shaped support such that the fabric of the sleeve can be secured to the valve tissue by suturing or stapling the fabric of the sleeve to the valve tissue. The collar may also provide a seal that prevents leakage of blood between the two sides of the heart valve.

According to a second aspect of the invention there is provided a method for producing a medical device. The method comprises the steps of: providing a first loop-shaped support, which is configured to abut a first side of the heart valve, providing a fabric sleeve, at least partly covering said first loop-shaped support with said sleeve, and forming at least a first flange by folding at least a portion of said sleeve over itself for forming a double layer of opposing fabrics thereof.

According to a further aspect of the invention there is provided a method for repairing a heart valve comprised of valve tissue including an annulus and a plurality of leaflets for allowing and preventing blood flow, the method comprising: inserting a device comprising at least one loop-shaped support and at least one flange unit being connected to the loop-shaped support to a heart valve, positioning the loop-shaped support such that it abuts a first side of the heart valve, positioning the flange unit such that it abuts the annulus, and fixating the device by attaching the flange unit to the annulus. The flange may comprise a fabric sleeve covering the loop-shaped support that is sutured, stapled, or otherwise attached to the annulus and thereby fix the device in place.

The method may comprise folding at least a portion of said sleeve over itself for forming a double layer of opposing fabrics thereof, such that said sleeve comprises a flange portion extending from said first loop-shaped support configured to overlap a surface of, and form a collar around, at least a portion of said annulus.

The method may further comprise the steps of: extending said flange portion of said sleeve away from said first loop-shaped support to form a flange overlapping a portion of said annulus and attaching said flange to said annulus.

The device may be inserted in o the heart valve by using a catheter, whereupon the catheter is withdrawn leaving the device in said heart valve.

The method may further comprise the step of sealing said flange unit against said annulus with a sealing surface of said flange unit before securing the device. The sealing said flange unit against said annulus may reduce or eliminate paravalvular leakage from a ventricle side to said atrial side of said heart valve by said sealing.

The method may further comprising the step of reducing or preventing a backflow of blood from a ventricle side to said atrial side of said heart valve by said sealing.

The advantages provided by a device having a flange unit have previously been described hereinabove. The inventive method for repairing a heart valve uses a corresponding device, whereby at least the same benefits are achieved.

The flange unit may be attached to the annulus by sutures or clips for a quick and easy fixation using well established means. Alternatively, or in addition, barb elements or tissue adhesives may be used for the attachment to the annulus.

The provision of a flange unit implies that a smooth transition section may be formed between the outer periphery of the device and annulus. Further, the flange unit presents a well defined and easy detectable surface for attachment of the clips or sutures. A smooth transition section as well as a well defined attachment surface allows for a smooth formation and growth of endothelia. Endothelia formation may further be improved by an endotheliazation agent. For a flange unit comprising a fabric sleeve, the endothelialization agent may be impregnated in or applied to a surface of all or a potion of the fabric and/or the fibers of the sleeve.

The flange unit may be conformed to the annulus before fixating the device. By conforming the flange unit, the transition section may be additionally smoothened, further enhancing growth of endothelia.

The device may be inserted to the heart valve by using a catheter, whereupon the catheter is withdrawn leaving the device.

In the method the first side of the heart valve may be the atrial side.

Further, in another aspect, the invention provides a kit comprising a device for improving the function of a heart valve comprised of valve tissue including an annulus and a plurality of leaflets, the device comprising: a first loop-shaped support, which is configured to abut a first side of the heart valve, and a first flange unit being connected to the first loop-shaped support, and which is configured to be arranged against the annulus when the first loop-shaped support is abutting the heart valve, and an artificial valve.

This device may be used in a medical procedure to perform annuloplasty, i.e. to reshape the valve annulus, in order to improve the function of the valve. The flange unit provides a well defined surface to be used when fixating the device against the annulus. This implies that the device may be fixated to the annulus very easily and in a speedy manner. The latter is of importance, since during heat surgery, a premium is placed on reducing the amount of time used to replace and repair valves as the heart is frequently arrested and without perfusion. Also, the flange unit provides a sealing surface against the annulus allowing prevention of backflow of blood from the ventricle side to the atrial side. The number of steps and time required for valve replacement surgery are reduced by the device carrying an artificial prosthetic valve. Additionally, the positioning of the prosthetic valve in relation to the annulus is facilitated.

The device may further comprise a second loop-shaped support, which is configured to abut a second side of the heart valve opposite to the first side, whereby a portion of the valve tissue is trapped between the first and second supports. The trapping of valve tissue between the first and second loop shaped supports implies that the desired shape of the valve may be fixated. Further, the trapping implies that the device may temporarily be kept in correct position while substantially fixating the device permanently to an annulus by means of e.g. sutures or clips.

The first loop-shaped support may be continuous with the second loop-shaped support to form a coil-shaped body. This implies that the device and its coil-shape may be applied at a commissure between the leaflets of the heart valve and be rotated 360° such that one loop-shaped support is inserted through the commissure to extend along one side of the valve and the other loop-shaped support being arranged along the opposite side of the valve. Thus, valve tissue will be trapped between the supports to fixate a desired shape of the valve. Depending on the extension of the flange means, the latter may provide an attachment surface on one of or on both s des of annulus for fixation of the device.

The first flange unit may extend from the first loop-shaped support to the second loop-shaped support, whereby the flange unit may be configured to be arranged against the annulus on opposite sides of the valve tissue being trapped between the first and second supports. This implies that the flange unit may form a surface on both sides of the heart valve, which surface may be used for fixation, not only of the device but also of a prosthetic valve. Further, the flange unit may form a sealing surface that, depending on the position of the device, allows prevention of possible backflow of blood from the ventricle side to the atrial side.

The second loop-shaped support may comprise a second flange unit being connected thereto, which flange unit may be configured to be arranged against the annulus on a side thereof being opposite the first loop-shaped support when the second loop-shaped support is abutting the heart valve. This allows prevention of paravalvular leakage.

At least one of the first and second flange units may have an intermittent or continuous extension along the periphery of its corresponding loop-shaped support. By way of example, in case of an intermittent extension the flange unit may be formed by two local sections diametrically opposing each other, whereby the two sections, when the device is positioned in the heart valve, are abutting the comrnissures forming a sealing surface thereto.

At least one of the first and second flange units may be made of a fabric material. A fabric has the advantage that it presents a rough surface enhancing growth of endothelia. Further, a fabric is easily penetrated by sutures or clips. Also, a fabric allows the flange unit to be easily conformed to the annulus.

Further, at least one of the first and second flange units may comprise a reinforcing element. The element provides an indication and definition of the area in which clips or sutures are to be put when fixating the device to the annulus. Further, the element reduces the risk of pockets being formed along the circumferential surface. Also, the element prevents unthreading of the fabric in the flange.

At least one of the extend out from and form below a diametric plane supports. By the flange first and second flange units may an angle of 30-60°, such as 40-50° formed by one of the loop-shaped unit initially extending below the diametric plane, the visibility during insertion is enhanced.

At least one of the first and second flange units may extend radially inwards or outwards from its corresponding loop shaped support.

The artificial prosthetic valve may be arranged on one of the loop-shaped supports. In the case the device is intended to be inserted to the heart from the atrial side, the artificial valve is preferably arranged on the support intended to be positioned on the atrial side of annulus and vice verse.

Further, in another aspect, the invention may relate to a method for replacing a heart valve comprised of valve tissue including an annulus and a plurality of leaflets for allowing and preventing blood flow, the method comprising: inserting a device comprising an artificial valve, at least a loop-shaped support and at least one flange unit being connected to the loop-shaped support to a heart valve, positioning the loop-shaped support such that it abuts a first side of the heart valve, positioning the flange unit such that it abuts the annulus, and fixating the device by attaching the flange unit to the annulus.

The advantages provided by a device having a flange unit and an artificial valve have previously been discussed above. The inventive method for replacing a heart valve uses a corresponding device, whereby the same benefits are achieved.

The flange unit may be attached to the annulus by using suitable fixation units, e.g. sutures or clips, which allows for a quick fixation using well established means.

The flange un t may be conformed to the annulus before fixating the device. By conforming the flange to the annulus, the surface to be covered by endothelia is reduced, allowing the growth to be enhanced and accelerated.

The device may be inserted to the heart valve by using a catheter, whereupon the catheter S withdrawn leaving the device.

In the method, the first side of the heart valve is preferably the atrial side.

The artificial valve may be arranged on one of said loop shaped supports.

Further embodiments of the invention are defined in the dependent claims, wherein features for the second and subsequent aspects of the invention are as for the first aspect mutatis mutandis.

Some embodiments of the invention provide for a reduced amount of time used to repair and/or replace cardiac valves.

Some embodiments of the invention also provide for a reduced or prevented backflow of blood, e.g. by a smooth transition section formed between the outer periphery of the device and annulus.

Some embodiments of the invention provide for a more convenient repair, e.g. by means of a well defined surface for attachment of fixating means such as sutures or clips.

Some embodiments of the invention provide for a smooth formation and growth of endothelia.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1a schematically illustrates a patient with a heart shown in cross-section and a device of an embodiment of the present invention schematically illustrated as supporting the mitral valve.

DETAILED DESCRIPTION OF THE INVENTION

Figure 1:
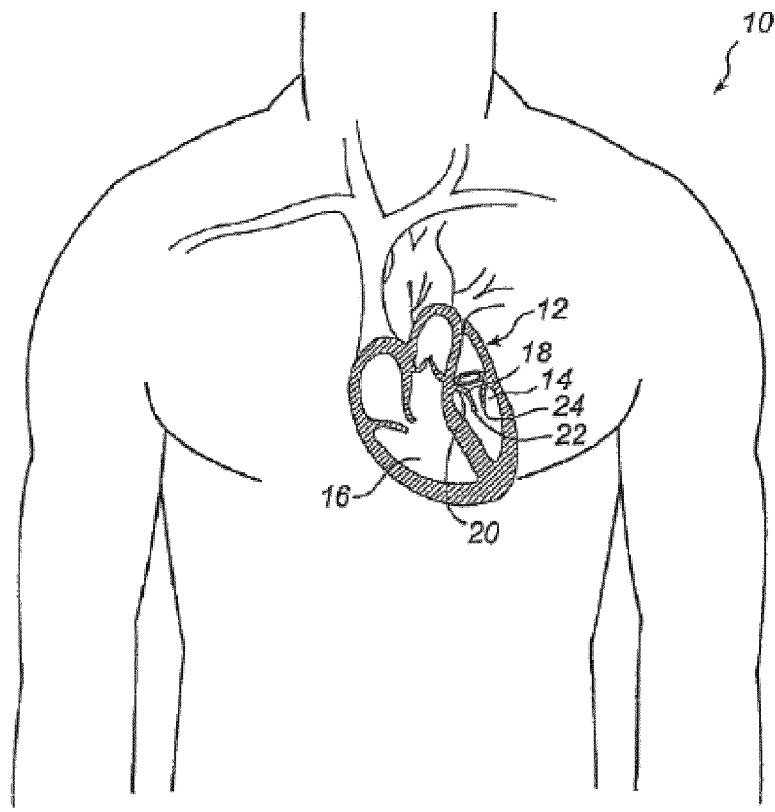
FIG. 1b is a cross-sectional view of the left ventricle showing the mitral valve in perspective.
Figure 1:
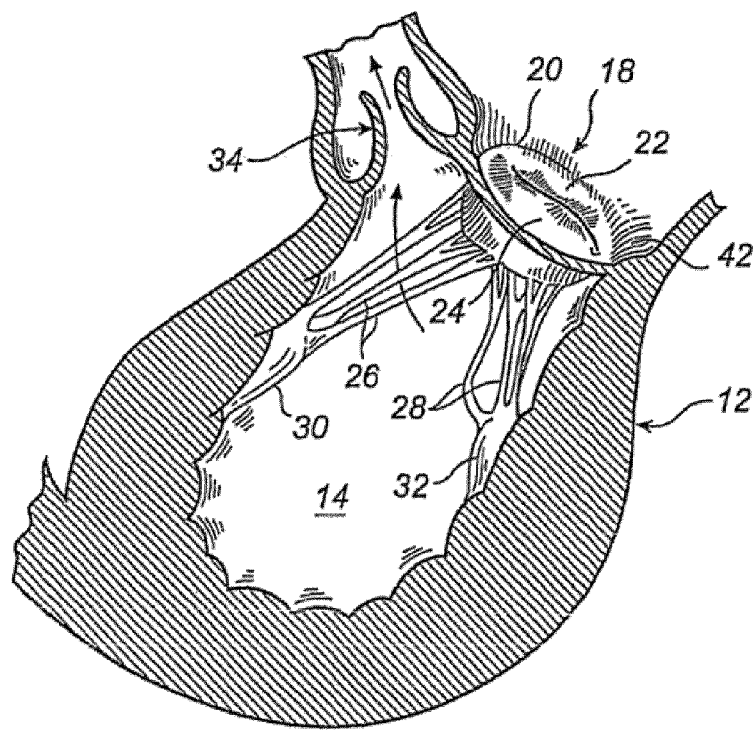

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated 5 in the accompanying drawings is not intended to be limiting of the invention. In the drawings, like numbers refer to like elements.

FIG. 1A illustrates a patient 10 having a heart 12 shown in cross-section including a left ventricle 14 and a right ventricle 16. The concepts of the present invention are suitable to be applied, for example, to a mitral valve 18, which supplies blood into left ventricle 14. Mitral valve 18, as better shown in FIG. 1B, includes an annulus 20 and a pair of leaflets 22, 24 which selectively allow and prevent blood flow into left ventricle 14. It will be appreciated that the term valve tissue is used extensively throughout this disclosure in reference to the drawings. The inventive principles are equally applicable when referring to any valve tissue such as annulus tissue, leaflet tissue or other attached vessel tissue. Leaflets 22, 24 20 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present 25 invention is applicable to tricuspidal heart valves as well.

Figure 2:
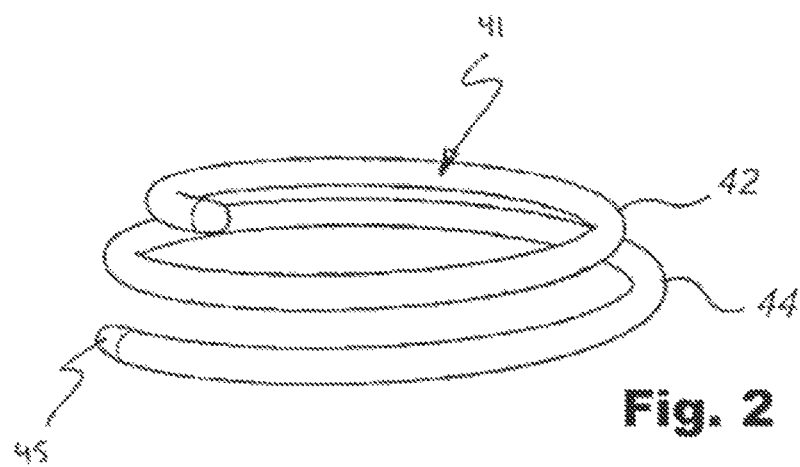
FIG. 2 is a perspective view of a body of a device according to a first example of the invention.
Figure 3:
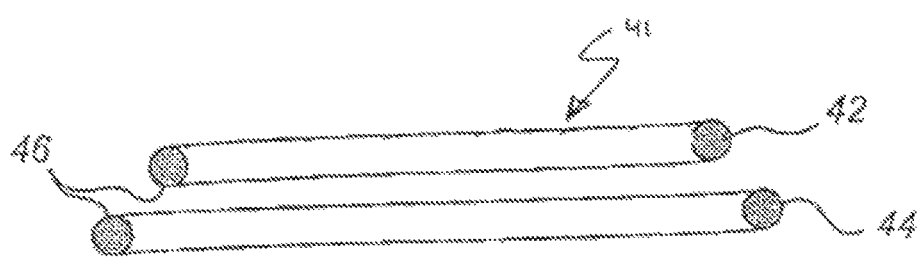
FIG. 3 is a cross-sectional view of the body in FIG. 2.

A body 41 comprised in a device 40 according to a first example of the present invention is shown in FIGS. 2 and 3. The body 41 comprises a first and a second loop-shaped support 42, 44.

As used herein, the term "loop-shaped" should be construed as a curved shape that may be closed, as at least a part of a ring with e.g. a circular, elliptic, or D-shaped form or any other closed form which may fit the shape of the valve annulus. The term "loop-shaped" also includes a curved shape that is open forming an arcuate shape, such as a C-shape or U-shape, which includes an angular turn of at least 180 0 such that the support may abut valve tissue along a major part of the annular valve shape. The term "loop-shaped" also includes a curved shape overlapping itself to form a portion of a coil. The term "loop-shaped" also includes three-dimensional curves.

The loop shape of at least a part of at least one of the supports 42, 44 may also in some embodiments be patient configured. The shape may be designed specifically to an anatomy of a patient. The patient specific loop shape may be virtually derived from 3D patient data, e.g. acquired by image modalities, such as Magnet c Resonance (MR) or Computer Tomography (CT) Imaging.

In co-assigned U.S. Pat. Nos. 6,419,696, 6,730,121, 6,964,684, and WO 2006/091163, which are incorporated by reference herein in their entirety for all purposes, devices are disclosed for repairing and replacing a heart valve in various embodiments. The devices include at least first and second support rings connected together in loop-shaped configurations to abut opposite sides of a valve annulus. A replacement valve may be secured to the loop-shaped devices.

The first support 42 may be continuous and/or integral with the second support 44 such that the supports 42, 44 assume a coiled configuration in the form of a spiral or keyring-type configuration with two loops.

The second support b may have an outer boundary or extent which is greater in relation to the outer boundary of the first support 42. The supports 42, 44 may in an embodiment have corresponding shapes with the second support 44 being in larger scale than the first support 42. This is advantageous in creating a pinch of the valve tissue between the first 42 and second supports 44.

An end 45 of the second support 44, which will lead the coil during insertion of the device at the valve, may in an embodiment have a greater pitch than the rest of the coil. This implies that the leading end 45 of the coil during rotation into position in the valve will project from immediate contact with the valve tissue and, therefore, the risk that the coil is caught by the chords is diminished.

The body 41 is shown in cross-section in FIG. 3. The body 41 has in an embodiment at least partly a round cross-sectional shape. In other embodiments, the cross section of the body 41 may be substantially flat, oval, flattened and/or have flattened edges. The opposed surfaces 46 provide a pinch to trap valve tissue there between. A round cross-section is also advantageous in creating a pinch of the valve tissue which will not harm the leaflets in their movement during normal heart action.

The second loop-shaped support 44 is slightly displaced radially with respect to the first loop-shaped support 42. This implies that the first and second loop-shaped supports 42, 44 are not arranged directly on top of each other in some embodiments. The pinch between the first 42 and second supports 44 is therefore not sharply defined in a radial direction of the valve. This implies that a pinching force between the supports is not focused to a specific radial position of the valve. As a result, the pinching force does not affect the movement of the leaflets during normal heart action and there is a diminished risk of rupture in the leaflets at the pinch.

The supports may in some embodiments be interrelated in such manner that the outer boundary of the first support 42 has a diameter corresponding to a line through the centre of the second support 44. Thus, the supports 42, 44 may overlap somewhat such that tissue is not allowed to move through the pinch and the shape of the valve is maintained advantageously.

Further, the cross-section of the supports 42, 44 is substantially round, which also gives a soft contact between the supports and the valve tissue to further diminish the risk of rupture in the leaflets. The body 41 may be formed from a core of a rigid material, such as a metal, e.g., titanium, or plastic. Any suitable medical grade material(s) may be used.

The rigid material may provide a passive spring function such that the loops of the coil may be forced a small distance away from each other but will flex back towards each other when the force is released. The core of the body 41 may be coated by a softer layer, such as a textile.

The body 41 may alternatively be formed from a shape memory material. The body 41 will then assume a desired, programmed shape, when e.g. heated to a specific temperature. This allows the body 41 to be compressed or straightened of the form better suited for delivering during insertion and to assume a spiral shape when inserted at the heart valve. Also, the flange unit may be made of such a shape memory material, e.g. to provide a first, delivery shape and a second, delivered shape thereof.

Figure 4:
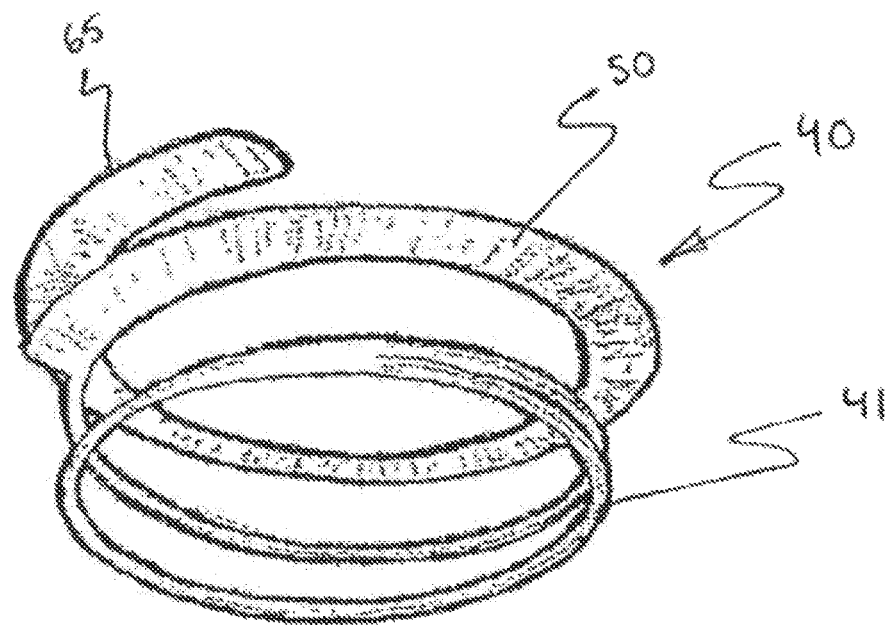
FIG. 4 is a perspective view of the first example of the device comprising the body shown in FIG. 2.
Figure 5:
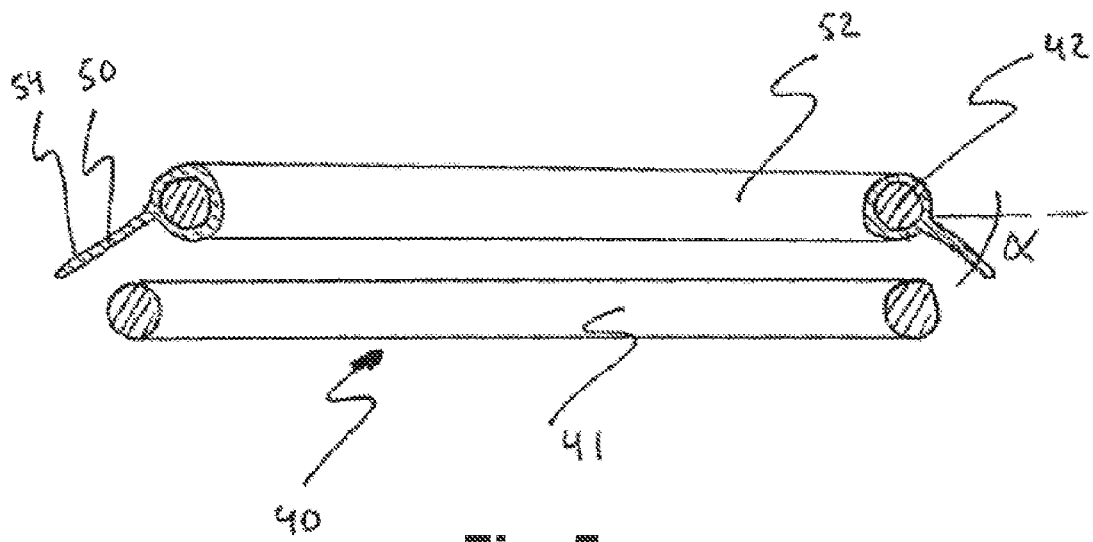
FIG. 5 is a cross-sectional view of the device in FIG. 4.

A first example of the medical device 40 is disclosed in FIGS. 4 and 5. The device 40 comprises a body 41 in accordance with that described above with reference to FIGS. 2 and 3. The device 40 comprises a flange unit 50 being connected to the body 41 and more precisely to the first loop-shaped support 42. The flange unit 50 has in an embodiment a continuous extension along the periphery of the first loop-shaped support 42.

Figure 16A:
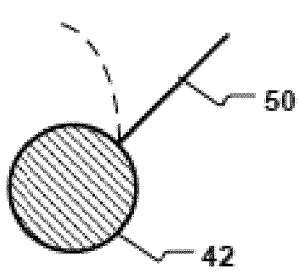
FIG. 16a, 16b are cross sectional views of examples involving a shape change.

In some examples, the flange unit 50 may be integral with at least a portion of the body 41, as e.g. shown in FIG. 16a. In some embodiments the flange unit 50 is made of a tube shaped flexible material 52 being passed onto the first loop-shaped support 42, whereby a loos substantially co-axial connection between the loop-shaped support and the flange unit is achieved. The connection may also be fixed or rigid. The flexible material may by way of example be a fabric or woven structure made of Polyethylene (PE) or polytetrafluoroethylene (PTFE). A fabric has the advantage that it presents a rough, holed or porous surface enhancing growth of and overgrowth of endothelia. Further, a fabric is easily penetrated by sutures or clips. In addition, the flexible material allows the flange unit 50 to be conformed to the annulus.

The flange unit 50 does in the disclosed embodiment form a flange surface 54 extending downwards out from the body. More precisely the flange unit 50 forms in some embodiments and angle α to a horizontal, diametric plane formed by the first loop shaped support. The angle α is approximately between 30-60°, such as 40-50° to the diametric plane. Such angle improves the visibility during insertion of the device. In some embodiments, improved visibility may be provided during insertion of the device, whereupon the flange unit 50 changes shape to a position facilitating fixation thereof to surrounding tissue. Thus, medical procedures for heart valve repair and/or replacement may be speeded up considerably.

In a practical embodiment the flange surface 54 has a width in the range of approximately 2-4 mm such as 2.5-3.5 mm. The width of the flange radially outwards allows an indication for the surgeon of the area in which sutures or clips should be positioned when fixating the device to the annulus. This is further discussed below with reference to FIG. 13. Initially, before inserted into the heart valve, the flange surface 54 extends downwardly. When positioned in the atrial side of the heart valve, the device will be arranged abutting the annulus whereby the flange unit will be conformed to the annulus, changing its angle from extending downwardly to extending upwardly. This ability to conform is a combination of the flexibility of the (fabric) material and the width of the flange means.

On its outer periphery, the flange unit 50 may comprise a reinforcing element 65, which is schematically illustrated in FIG. 4. Such reinforcing element may by way of example have the form of a thread or a bead.

Figure 18:
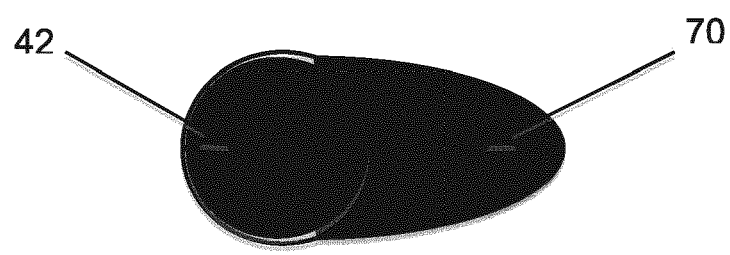
FIGS. 18a, 18b, and 18c show cross-sectional views of embodiments comprising a fabric flange unit.
Figure 18:
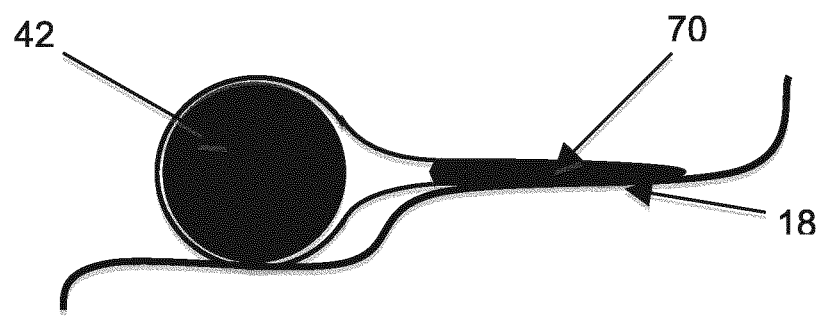
Figure 18:
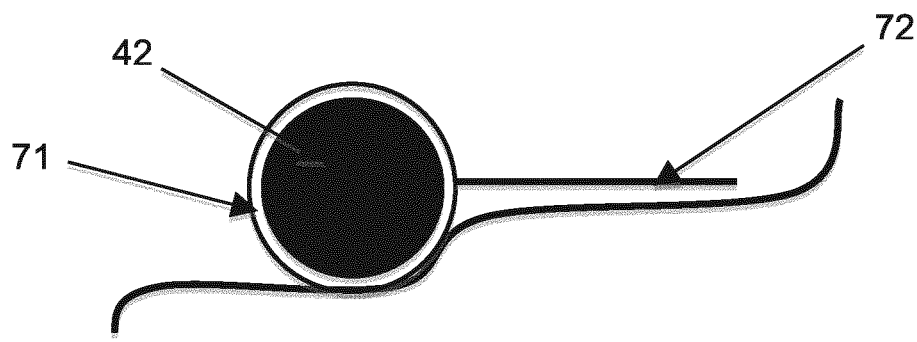

FIGS. 18a, 18b, and 18c show cross-sectional views of a loop-shaped support and a flange unit comprising a fabric sleeve 70 that covers the looped-shaped support 42.

The sleeve 70 can be positioned on an annuloplasty implant by sliding it onto one or more of loop-shaped supports 42, 44 from either end of the annuloplasty body. Alternatively, the sleeve 70 may be made from a flat piece of fabric (not shown) that is folded over the annuloplasty implant along its longitudinal axis. The lateral ends of the thus folded fabric may be sewn together or otherwise suitable attached to each other. This may e.g. be done using integrated fastening means in them upon longitudinally folding over, opposing fabric portions by fastening units. Fastening units may be of the hook and loop type fasting means allowing an easy assembly. This may be advantageous when the implant body has varying cross sections and the sleeve is only to be provided at a longitudinal portion intermediate ends of the implant and at a section with reduced cross section. In this manner, the sleeve may also be prevented from sliding longitudinally along the implant body without the need for longitudinal fixation units.

The longitudinal folded over section with opposing fabric sections may be provided as a pre-fabricated flange unit. That means the double layer of opposed fabrics may be provided as a substantially flat sub-section extending radially outwardly from at least a longitudinal portion of the support 42 and/or 44. The sleeve 70 may be closed at one end and designed with a specified length such that the open end of the sleeve is positioned at a desired location on at least one of the supports 42, 44 when the sleeve is slid into place and fully extended along a length of the support. The inner cross-sectional diameter of the sleeve 70 is greater than the cross-sectional diameter of the support such that the sleeve loosely covers all or a portion of the support 42 and/or 44 with enough slack in the sleeve 70 to allow the fabric of the sleeve to overlap a surface of the annulus 18 (FIG. 18b) and form a collar around a portion or all of the circumference of the annulus.

The sleeve, in some embodiments, is thus oversized in relation to the outer cross section of the annuloplasty implant, namely one or more of the supports 42 and/or 44. This may of illustrative reasons not be shown in all figures.

It should be noted that, even illustrations like FIGS. 5, 10, 13, 14a, 14b, 15, 16a, 16b, and 17, where the reader might have the impression that the sleeve appears to be a single layer, like in FIG. 18c, should note that embodiments falling under the illustrations have a folded over, double layer, in particular formed from an oversized sleeve as shown in FIGS. 18a-18b.

The loop-shaped support need not have a circular cross-sectional shape as shown in FIGS. 18a-c and may, for example have a cross-sectional shape as shown in FIGS. 4 and 6-9.

Different support element 42 and/or 44.

Alternatively, or in addition, a longitudinal section of the oversized sleeve may be partly flattened radially outwardly. Thus opposing fabric sections may be provided as a pre-fabricated flange unit allowing easy gripping, and an advantageous final shaping by the surgeon upon implantation. That means the double layer of opposed fabrics may with a fold over at the radial perimeter. The pre-fabricated sleeve portion is still provided on an oversized sleeve covering the support 42 and/or 44. The pre-fabricated sleeve portion may be provided as a substantially flat sub-section extending radially outwardly from at least a longitudinal portion of the support 42 and/or 44. By giving the at least first flange a final shaping upon implantation, it is possible to customize the medical device for different patients and thereby enable the provision of a medical device, which can fit well together with a larger variety of sizes of heart valves. Thus, a more flexible and versatile medical device has been achieved.

During placement of the annuloplasty device, the sleeve may be drawn radially away from the loop-shaped support to overlap valve tissue of the annulus as shown in FIG. 18b to form a flange. In some cases, the sleeve 70 may be drawn radially inward to overlap valve tissue in the annulus 18. In other cases, the sleeve may be drawn away from the loop-shaped support 42 in more than one direction to form more than one flange, for example a flange along the outer edge of the looped shaped support and a flange along the inner edge of the loop-shaped support 42.

The fabric between the annulus and support may then be tensioned while the flange portion of the sleeve 70 is secured to valve tissue in the annulus by suturing, clamping, or stapling the fabric of the sleeve 70 to the valve tissue. Securing the sleeve 70 to the valve tissue of the annulus fixes the annuloplasty device in place and may optionally provide a seal that prevents leakage of blood between the two sides of the heart valve. The outer edge of the fabric may optionally be folded back over itself one or more times before being sutured or otherwise secured to the annulus 18.

FIG. 18*c* shows an alternative embodiment in which the sleeve 70 may be configured to comprise a casing portion 71 that fits over the loop-shaped support such that the sleeve may easily be slipped onto the support 42 or 44 from either end of the body 41. The casing may be closed at one end and designed with a specified length such that the open end of the casing portion is positioned at a desired location on at least one of the supports 42, 44 when the sleeve is slid into place with the casing portion fully extended. The sleeve 70 comprises a fabric flange portion 72 extending, usually outward, from casing 71. The fabric comprising flange portion 72 may have a single, constant thickness or a thickness that varies along the axial length of the sleeve and/or along the radial length from the loop-shaped support 42.

During placement of the annuloplasty device, the flange portion 72 of the sleeve may be drawn radially away from the loop-shaped support to overlap valve tissue of the annulus 18 to form a flange. In some cases, the flange portion 72 may be drawn radially inward to overlap valve tissue in the annulus. The fabric between the annulus and support may then be tensioned while the flange portion 72 is secured to the annulus 18 by suturing, clamping, or stapling the fabric of the flange portion 72 to the valve tissue. Securing the flange portion 72 to the valve tissue of the annulus fixes the annuloplasty device in place and may optionally provide a seal that prevents leakage of blood between the two sides of the heart valve.

A flange unit comprising a sleeve 70 with or without a casing 71 and a flange portion 72 has the advantage of being easy to manufacture and provides the option of placing the flange unit onto the annuloplasty device immediately before implantation. Additionally, the sleeve 70 or casing 71 fits loosely around the body of the annuloplasty device so that the tensioning of the fabric of sleeve 70 rotates the sleeve or casing around the loop-shaped support(s) 42, 44 and ensures that the rotational orientation of the flange with respect to the annuloplasty device body is correct. The fabric of the flange unit may advantageously be impregnated with, or have incorporated within it, one or more drugs. The flange unit may also advantageously be used as a site of attachment for a prosthetic heart valve to the annuloplasty devise.

Figure 6:
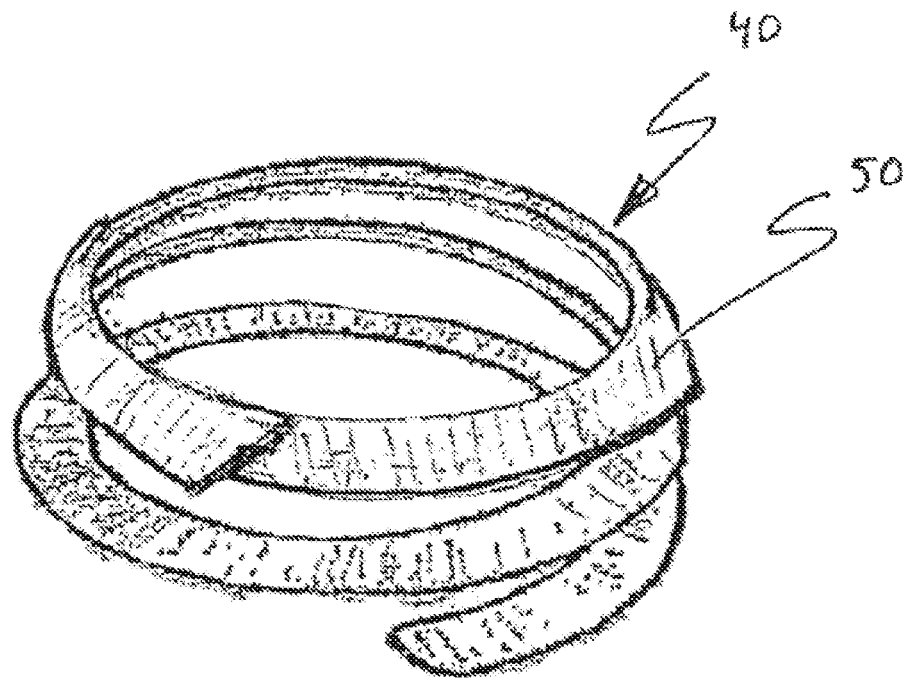
FIG. 6 is a perspective view of a second example of the device.

Now turning to FIG. 6, a variant of the device 40 is disclosed. The device differs from that disclosed in FIG. 4 and in that the flange unit 50 extends from the first loop-shaped support 42 to the second loop-shaped support 44. The flange unit 50 may be formed in one piece or be separated into a first and a second piece, wherein the first piece is connected to the first loop-shaped support and the second pieces connected to the second loop-shaped support. The connection may be a rigid connection or a loose connection. The latter may be achieved by the flange unit being passed onto the loop-shaped support(s).

The flange unit may be continuous or intermittent along its extension. The example is suitable no matter if the device is to be used for repairing or replacing a valve.

Figure 7:
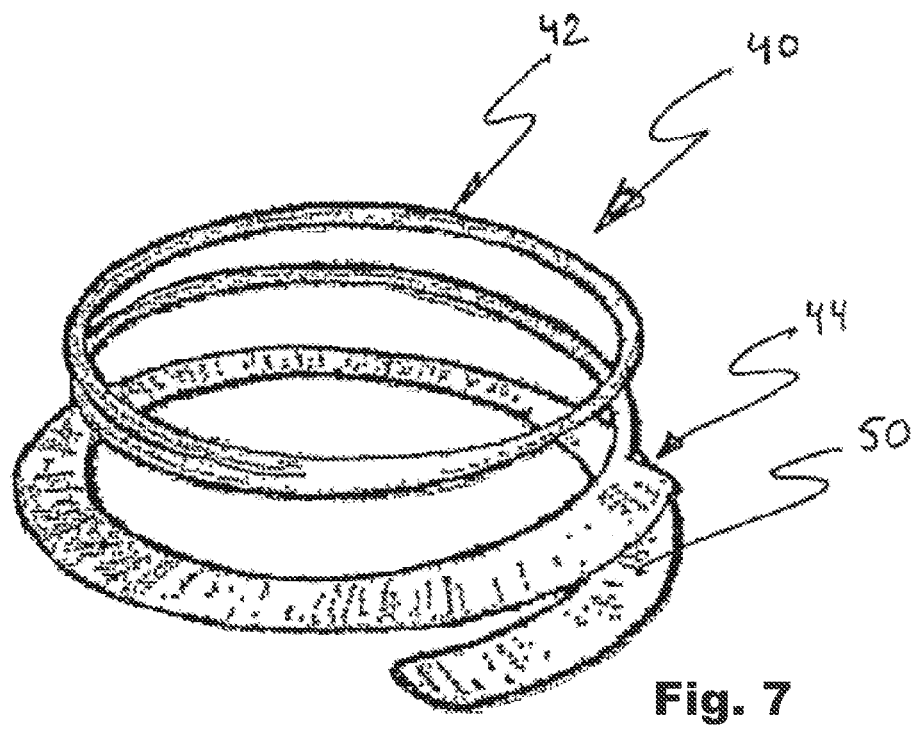
FIG. 7 is a perspective view of a third example of the device.

Now turning to FIG. 7, a third embodiment of the device 40 is disclosed. The device 40 differs from that disclosed in FIGS. 4 and 5 in that the flange unit 50 extends along the second loop-shaped support 44. When positioned in the heart valve, the second loop-shaped support 44 is intended to abut the ventricle side of the heart valve, whereas the first loop-shaped support 42 is intended to abut the atrial side. The flange unit 50 may be continuous or intermittent along its extension. The device may be suitable when used in valve replacement. An artificial, i.e. prosthetic valve may be carried by either the body or the flange means.

Figure 8:
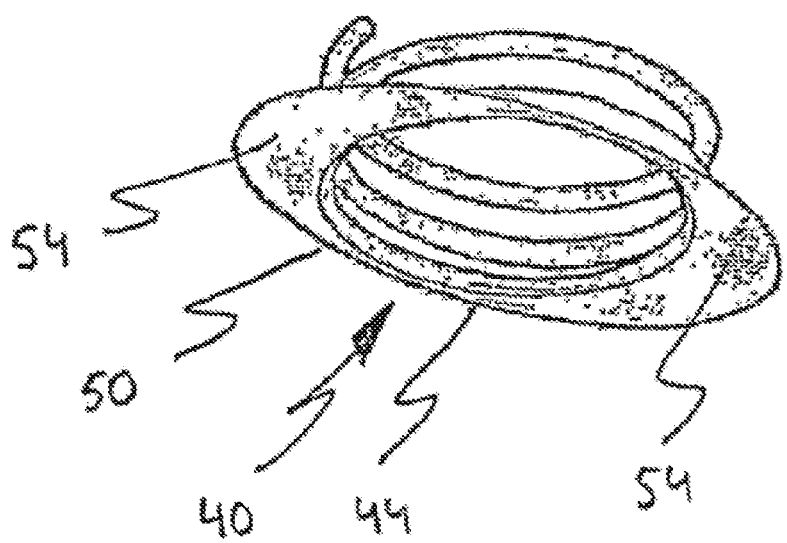
FIG. 8 is a perspective view of a fourth example of the device.

FIG. 8 shows another variant of the device 40. The device 40 differs from that disclosed in FIGS. 4 and 5 in that the flange unit 50 extends along the second loop-shaped support 44 and forms two flange surfaces 54, both being connected to the second loop-shaped support 44. The flange surfaces 54 are so arranged on the loop-shaped support 44 that they overlap the commissures when the device is arranged in the heart valve abutting the annulus. Thereby the two flange surfaces form a sealing preventing possible leakage of blood from the ventricle side to the atrial side.

In the above discussed embodiments of the device, the flange unit has been disclosed as being either continuous or intermittent along its extension. The flange unit may further have a non-uniform width varying along its extension. By way of example the width may be larger in a region corresponding to a position overlapping the commissure when the device is arranged in the heart valve abutting the annulus.

Figure 9A:
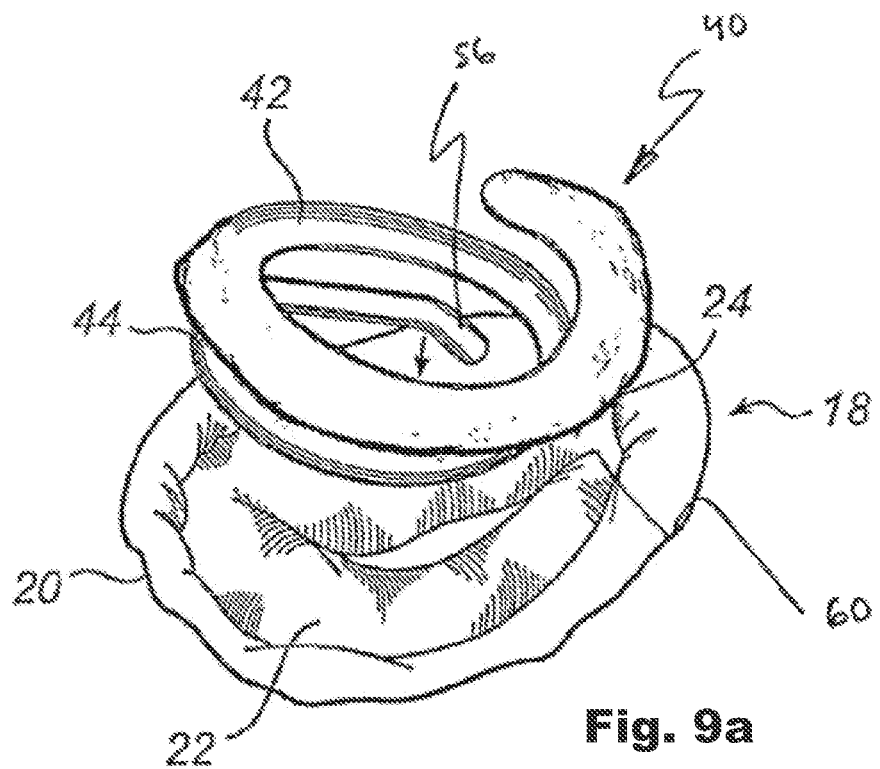
FIG. 9a, 9b are perspective views that illustrate insertion of an example of the device.
Figure 9B:
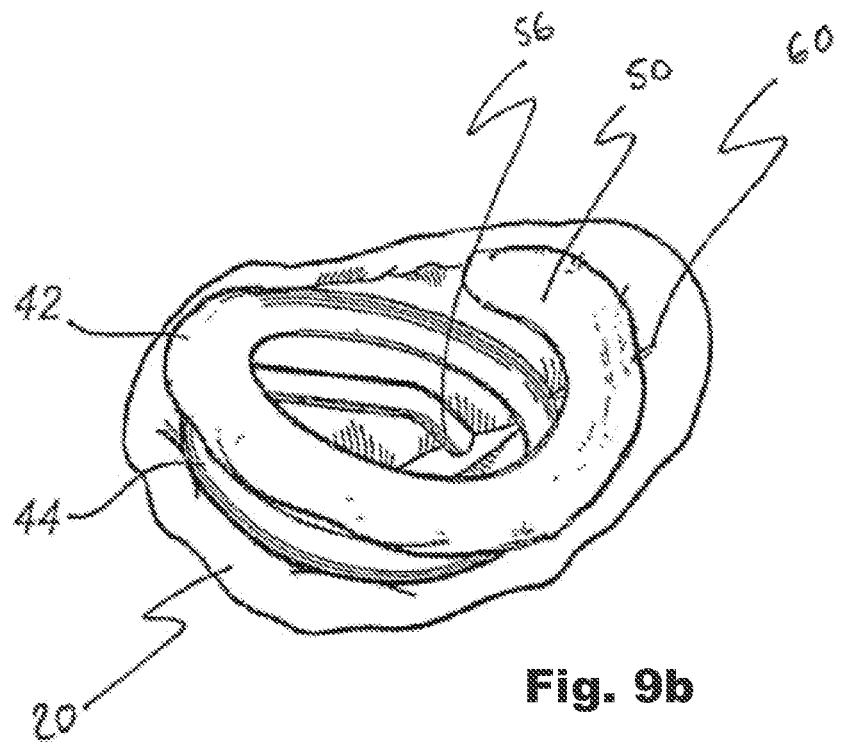
Figure 10:
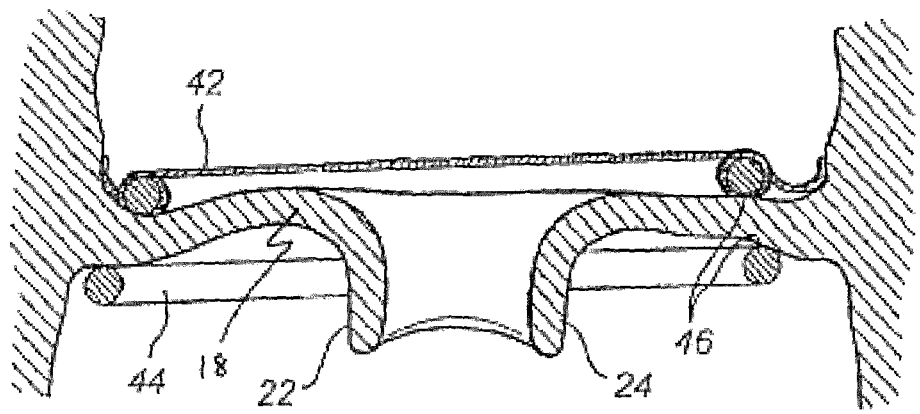
FIG. 10 is a cross-sectional view showing an example of the device inserted in a heart valve.
Figure 11:
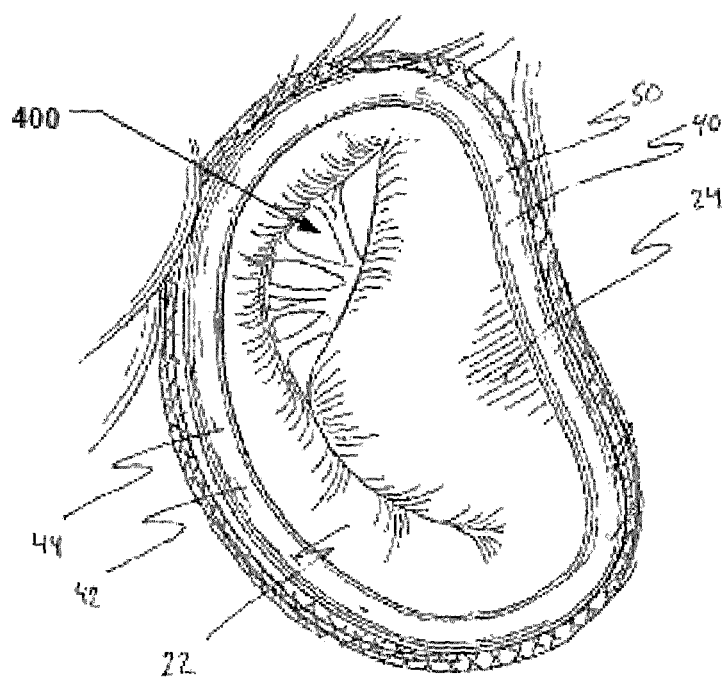
FIGS. 11 and 12 are schematic illustrations that show a heart valve before and after remodelling by using the device.

Referring now to FIGS. 9-11, a method for repairing a heart valve will be described.

First, access to the heart valve is achieved by conventional techniques, including arresting the heart and opening the chest. Alternatively, an intraluminal catheter based delivery technique may be applied. In FIG. 9*a*, the device 40 is shown when being inserted to the mitral valve 18 from the atrial side. The device 40 is being carried on a carrier or tool (not shown), which is connected to a stem for remote control of the positioning of the carrier. An end 56 of the second loop-shaped support 44 is brought to the opening of the mitral valve 18 at a commissure 60 between the leaflets 22, 24, as shown in FIG. 9*b*. The end 56 is led through the opening and the carrier is turned 360 degrees. Thus, the second support 44 will be rotated into place on one side of the valve 18, whereas the first support 42 and the flange un s placed on the opposite side of the valve 18. During this rotational movement the flange unit 50 is deflected from its original direction forming an angle of 30-600 downwards from the diametric plane formed by the support 42 to a direction extending in an angle upwards from the diametric plane corresponding to the wall formed by the annulus 20. The deflection allowed by the flexibility of the flange unit 50 results in a close abutment between the flange unit 50 and the atrial side of the annulus 20. If necessary, the flange unit 50 may be additionally conformed to the annulus 20. In this way, the device 40 is arranged in engagement with the valve 18, as shown in FIG. 10.

Figure 12:
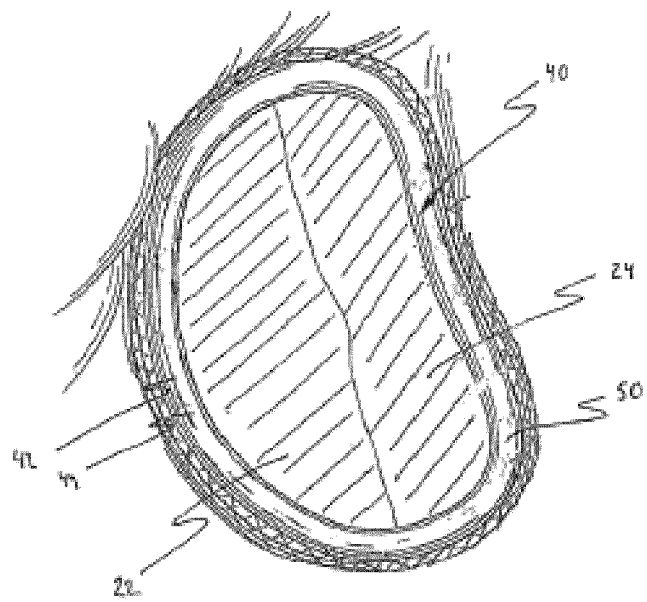

Further, the supports 42, 44 are placed on opposite sides of the valve 18 pinching valve tissue between them to maintain a shape of the valve 18. The leaflets 22, 24 may now be drawn towards each other through the pinch of the support rings 42, 44 so as to remodel the shape of the valve 18. The leaflets may be drawn through the pinch by means of a forceps instrument. The supports 42, 44 may flex away from each other to allow drawing leaflets 22, 24 through the pinch and towards each other for preventing the leaflets 22, 24 to slip back. The valve annulus 20 may in this way be remodeled and the new shape is maintained by the supports 42, 44, see FIGS. 11 and 12 showing before and after remodelling. In FIG. 11 a defective closure region 400 of the valve leaflets 22, 24 is shown. The supports 42, 44 may have roughened, opposed surfaces 46 to better keep the leaflets 22, 24 from slipping through the pinch and to hold the valve annulus 20 in its reshaped form.

Figure 13:
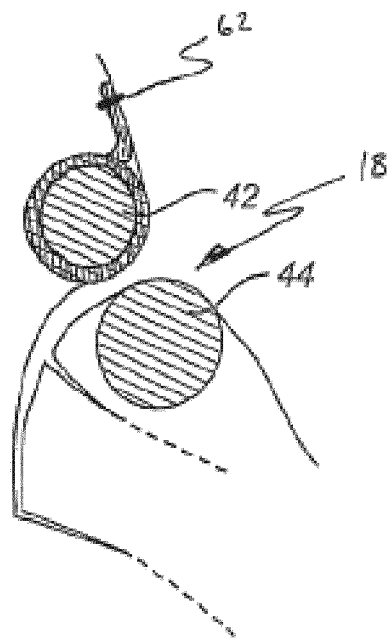
FIG. 13 is a cross sectional view that shows the device fixed to the annulus.

The device 40 may now be secured to the valve 18 for strengthening the fixation of the relative position between the supports 42, 44 and the valve tissue, see FIG. 13. The fixation may be made by clips or sutures 62 which are arranged through the flange unit 50 and its circumferential flange surface 54. By the latter being made of fabric it is easily penetrated. The clips or sutures 62 are preferably oriented and positioned in the circumferential direction of the flange unit 50. The number of fixation points is arbitrary for the provision of a durable fixation.

The flange unit 50 provides in some embodiments a better seat and prevents sliding of the device 40. Thus, the device 40 is positioned more stable in the procedure, which is advantageous, especially for long-term performance of the device after insertion.

As illustrated in FIG. 10, the second support 44 is slightly displaced radially with respect to the first support 42. This implies that the first and second supports 42, 44 are not arranged directly on top of each other. The pinch between the first and second supports is therefore not sharply defined in a radial direction of the valve. This implies that a pinching force between the supports is not focused to a specific radial position of the valve. As a result, the pinching force does not affect the movement of the leaflets during normal heart action and there is a diminished risk of rupture in the leaflets at the pinch. The supports are interrelated in such manner that the outer boundary of the first support 42 has a diameter corresponding to a line through the centre of the second support 44. Thus, the supports 42, 44 overlap somewhat such that tissue is not allowed to move through the pinch and the shape of the valve is maintained. Further, the cross-section of the supports 42, 44 is round, which also gives a soft contact between the supports and the valve tissue to further diminish the risk of rupture in the leaflets.

The method described above is applicable no matter the shape, position or extension of the flange means. Further, the method is applicable no matter if the device is inserted from the atrial side or the ventricle side.

A device having a flange unit on the first, upper loop-shaped support is suitable when the device is to be positioned on the atrial side, providing a fixation surface to the atrial side of the annulus. Such device is also suitable when carrying an artificial valve. Further, a device having a flange unit on the second loop-shaped support is suitable when the second loop shaped support is to be positioned on the ventricle side of the heart valve.

A device having a flange unit extending from the first to the second loop-shaped support is suitable no matter if the device is positioned on the atrial side or the ventricle side of the heart valve.

Figure 14A:
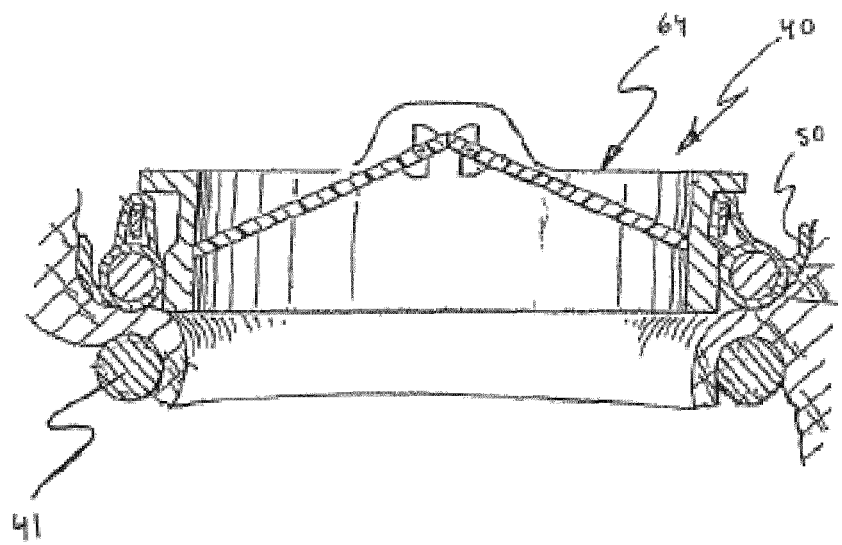
FIG. 14a is a cross sectional view that shows a first example of the device comprising an artificial prosthetic heart valve.
Figure 14B:
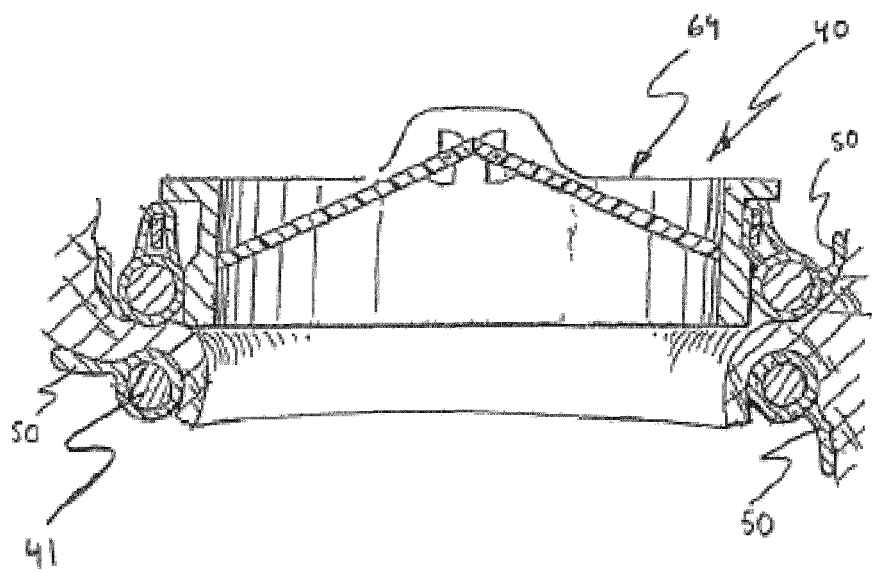
FIG. 14b is a cross sectional view that shows a second example of the device comprising an artificial valve.
Figure 15:
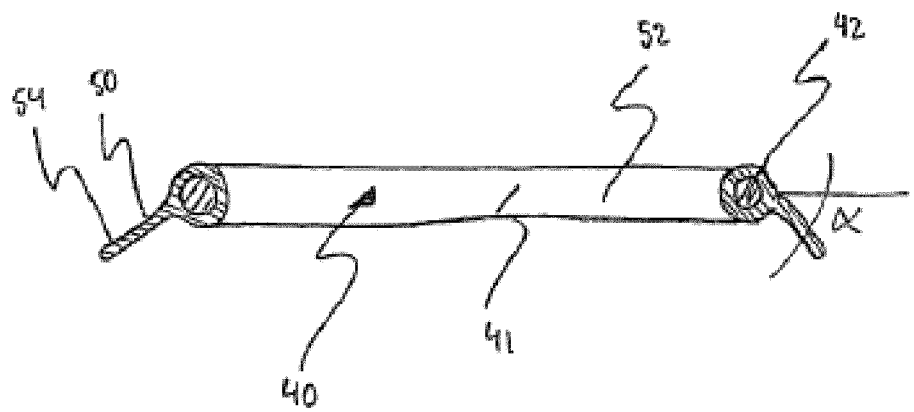
FIG. 15 is a cross-sectional view of an alternative device having one loop-shaped support carrying the flange unit.

With reference to FIG. 14a and FIG. 14b, it is to be understood that the device may be used for replacement of heart valves as well. For that purpose the device 40 comprises in addition to a body 41 and a flange unit 50 an artificial valve 64. The flange unit 50 may be carried by the first loop shaped support 42 as is shown in FIG. 14a. Alternatively, as is shown in FIG. 14b, the flange unit 50 may extend from the first 42 to the second 44 support. Although not shown, it is to be understood that each support 42, 44 may carry its own flange unit 50, or that the flange unit may be carried by the second support 44 only.

The method of inserting, positioning and fixation of the device is generally the same as that used when repairing a heart valve, whereby the method as such is not further discussed.

It should be emphasized that the preferred embodiments described herein are in no way limiting and that many alternative embodiments are possible within the scope of protection defined by the appended claims.

By way of example, the device 40 and its body 41 has been disclosed as having a first 42 and a second 44 loop-shaped support. The device 40 is applicable with only one loop-shaped support carrying the flange unit 50. One such embodiment is disclosed in FIG. 15.

Further, the access to the heart valve may be achieved endoscopically, or transluminally, catheter based. In such case, the device 40 needs to be inserted through a narrow tube (endoscope or catheter). This implies that the device 40 will need to be compressed during insertion in order to pass through the endoscope or catheter. The device 40 needs to assume its proper shape after having been passed through the endoscope. Therefore, using an endoscopic or catheter based approach, the body may advantageously be formed from a shape memory material. This allows the device 40 to be compressed and also to have a stable shape when being applied to the heart valve. In an alternative, the access to the heart valve may be achieved through a catheter, which is passed through the vascular system to the heart. In this case, the supports may be formed from a shape-memory material, which during insertion extends along the catheter in a flexible state and, when pushed out of the catheter at the heart valve, assumes a pre-stressed coil-shape in order to abut the heart valve on opposite sides.

The first and second loop-shaped supports may be connected to each other by means of a connect ng part so as to form a coil-shape. The coil-shape of the device is advantageous during insertion, since the device may then be rotated into position, as described above. However, the connecting part is detachable from at least one of the supports. Thus, when the device has been inserted, the connecting part may be detached and removed from the opening of the valve.

The loop-shaped support(s) and the flange unit may be provided as separate parts. Further, it is to be understood that the flange means, or at least a wing part thereof, may form an arbitrary angle to its corresponding loop-shaped support.

Figure 16B:
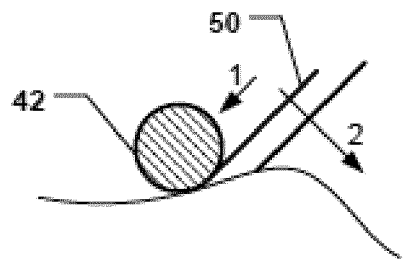

FIG. 16a, 16b are cross sectional views of embodiments involving a shape change. In FIG. 16a the change of shape of a flange unit 50 is illustrated, e.g. for being out of a line of sight for a surgeon during insertion (dotted line) and, when in contact with body tissue, turning to a second shape (continuous line) for attaching to the tissue.

In FIG. 16a the change of shape of a flange unit 50 is illustrated in two steps or directions. Firstly the flange unit may shrink in a first direction, in order to eliminate any wrinkles or folds therein. Subsequently or concurrently, the flange unit 50 may change shape in a second direction, e.g. as described with reference to FIG. 16a.

Figure 17:
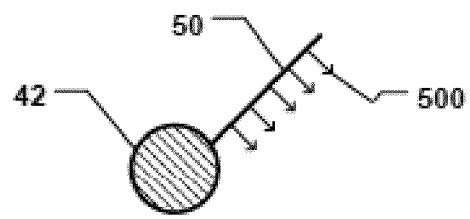
FIG. 17 is a cross sectional view schematically illustrating a flange unit having barb elements for affixing to tissue.

FIG. 17 is a cross sectional view schematically illustrating a flange unit 50 having barb elements 500 for affixing the device 40 to tissue. The flange unit 50 may thus be a carrier for fixation elements. The flange unit 50 may thus be inserted into the body more effectively.

In some embodiments, different materials may be used for parts of the device 40. For instance, the inner rings 42, 44 may be made of a stiffer more stable than a more flexible outer part, e.g. the flange unit 50.

In addition, or alternatively, in some embodiments (not shown) the double layer flange unit may be folded over towards the center of the device. The flange unit may additionally be provided with reinforcement sections or units, such as disclosed in European Application number EP11188656.0 and U.S. Provisional Patent Application Ser. No. 61/558,787, both of the same inventor as the present disclosure, and entitled "A DEVICE AND A METHOD FOR IMPROVING THE FUNCTION OF A HEART VALVE", which are incorporated herein by reference in their entirety for all purposes. The reinforcement sections or units comprise more particularly one or more flexible leaflet reinforcement patch(es). A flexible leaflet reinforcement patch may thus be provided as a double layer fabric, which is configured to provide reinforcement to at least one of the leaflets.

While several embodiments of the present invention have been described and illustrated herein, hose of ordinary skill in the art will readily envision a variety of other means and/or structures for performing the functions and/or obtaining the results and/or one or more of the advantages described herein, and each of such variations and/or modifications is deemed to be within the scope of the present invention as defined by the enclosed claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention as limited by the appended patent claims.

A device for improving the function of a heart valve comprises a first loop-shaped support, which is configured to abut a first side of the heart valve. A first flange unit is may be configured as a fabric sleeve covering the loop-shaped support. A portion of the fabric sleeve forms a flange that is attached to then annulus when said first loop-shaped support is abutting said heart valve. The flange is provideable by folding at least a portion of said sleeve over itself for forming a double layer of opposing fabrics thereof, such that said sleeve comprises a flange portion extending from said first loo-shaped support configured to overlap a surface of, and form a collar around, at least a portion of said annulus.

What is claimed is:

1. A method for repairing a heart valve, said heart valve comprising valve tissue including an annulus and a plurality of leaflets, said method comprising:
    inserting a medical device into said heart valve, said medical device comprising first and second loop-shaped supports, and a fabric sleeve at least partly covering the first loop-shaped support, wherein the first loop-shaped support is continuous with the second loop-shaped support to form a coil-shaped body;
    positioning the first loop-shaped support such that it abuts a first side of the heart valve,
    positioning the second loop-shaped support such that it abuts a second side of the heart valve, opposite the first side, to trap a portion of the valve tissue between the first and the second loop-shaped supports,
    positioning a flange unit comprising first and second flat flanges such that it abuts said annulus comprising
        drawing the fabric sleeve from the first loop-shaped support in more than one direction to form the first and the second flat flanges comprising double layers opposed fabrics, comprising
            drawing the fabric sleeve to form the first flat flange along an outer edge of the first loop-shaped support, and
            drawing the fabric sleeve to form the second flat flange along an inner edge of the first loop-shaped support,
    wherein an inner cross-sectional diameter of the fabric sleeve is greater than a cross-sectional diameter of the first loop-shaped support such that the fabric sleeve loosely covers all, or a portion, of the first loop-shaped support with enough slack in the fabric sleeve such that fabric of the fabric sleeve is configured to form the first and the second flat flanges; the fabric sleeve thus being oversized in relation to the cross-sectional diameter of the first loop-shaped support; and
    securing said device by attaching said flange unit to said annulus.

2. The method according to claim 1, comprising drawing the fabric sleeve radially away from the first loop-shaped support to overlap a portion of the annulus.

3. The method according to claim 1 comprising drawing the fabric sleeve radially inward from the first loop-shaped support to overlap the valve tissue.

4. The method according to claim 1, wherein the medical device is inserted into the heart valve by using a catheter, whereupon the catheter is withdrawn leaving the medical device in said heart valve.

5. The method according to claim 1, comprising folding the fabric sleeve back over itself one or more times before being secured to the annulus.

6. The method according to claim 1, comprising rotating the fabric sleeve around the first loop-shaped support upon said drawing of the fabric sleeve from the first loop-shaped support in more than one direction.

7. The method according to claim 1, comprising attaching a prosthetic heart valve to the fabric flange unit.

8. The method according to claim 1, comprising overlapping commissures of the heart valve with the flange unit.

9. The method according to claim 1, wherein the flange unit comprises a flexible leaflet reinforcement patch, the method comprising providing reinforcement to at least one of the leaflets with the flexible leaflet reinforcement patch.

10. The method according to claim 1, comprising impregnating the fabric sleeve with drugs.

11. The method according to claim 1, wherein said first side of the heart valve is the atrial side.

* * * * *